United States Patent [19]

Meiller

[11] 4,049,691

[45] Sept. 20, 1977

[54] AROMATIC AMINO SILANES AND THEIR POLYMERS

[75] Inventor: Francois Meiller, Palaiseau, France

[73] Assignee: Rhone-Progil, Courbevoie, France

[21] Appl. No.: 725,097

[22] Filed: Sept. 20, 1976

Related U.S. Application Data

[63] Continuation of Ser. No. 494,780, Aug. 5, 1974, abandoned.

[30] Foreign Application Priority Data

Aug. 17, 1973 France .................................. 73.29950

[51] Int. Cl.² .............................................. C07F 7/10
[52] U.S. Cl. ............................................ 260/448.2 N
[58] Field of Search .................................. 260/448.2 N

[56] References Cited

U.S. PATENT DOCUMENTS

| | | | |
|---|---|---|---|
| 2,823,218 | 2/1958 | Speier et al. ................... | 260/448.2 E |
| 2,970,150 | 1/1961 | Bailey ............................ | 260/448.8 R |
| 3,020,302 | 2/1962 | Bailey et al. .................. | 260/448.2 N |
| 3,375,218 | 3/1968 | Bailey et al. ............. | 260/448.2 N X |
| 3,678,089 | 7/1972 | Berger ....................... | 260/448.8 R X |
| 3,898,255 | 8/1975 | Meiller .......................... | 260/448.2 N |

OTHER PUBLICATIONS

Noll, "Chemistry and Technology of Silicones," 2nd Ed., Academic Press, N. Y. (1968), p. 81.

*Primary Examiner*—Paul F. Shaver
*Attorney, Agent, or Firm*—McDougall, Hersh & Scott

[57] ABSTRACT

Aromatic amino silanes having 1, 2 and 3 hydrolyzable groups and polymers thereof in which corresponding nitrophenols are hydrogenated in the presence of a catalyst at a temperature below 30° C in which compounds having 2 to 3 hydrolyzable groups produce polymers suitable for use in the preparation of silica and alumina grafts and the compounds having one hydrolyzable group are suitable for use as colorants and the synthesis of polymers.

9 Claims, No Drawings

AROMATIC AMINO SILANES AND THEIR POLYMERS

This is a continuation of application Ser. No. 494,780, filed Aug. 5, 1974, now abandoned.

The invention relates to aromatic amino silanes and polymers thereof. It also relates to a process for the preparation of the said silanes and polymers.

Aromatic amino silanes are products which are not well known, since the nitrated products necessary for their preparation are generally obtained by the conventional techniques of nitration, which in this case lead to mixtures of isomers which are difficult to separate.

The present invention has the purpose of obtaining aromatic amino silanes in the pure state and polymers thereof.

According to the invention the aromatic amino silanes are represented by the general formula

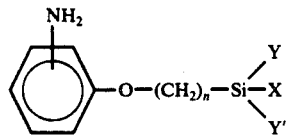

wherein:

$n$ is a whole number having a value of 2 to 4;

X represents a linear or branched alkoxy group possessing 1 to 8 carbon atoms;

Y and Y', similar to or different from one another, represent a methyl, ethyl, or phenyl group, or a linear or branched alkoxy group possessing 1 to 8 carbon atoms.

The silanes according to the invention, in which the alkoxy group or groups possess few carbon atoms or are branched, are in the form of distillable liquids. On the other hand, the silanes according to the invention in which the alkoxy group or groups are formed with a long straight chain can be in the form of solids.

The polymers of the above-defined silanes are products, the structure of which varies with the number of hydrolyzable substituents on the silicon atom of the silane:

If only X is a hydrolyzable substituent, the corresponding polymer is a dimer represented by the general formula

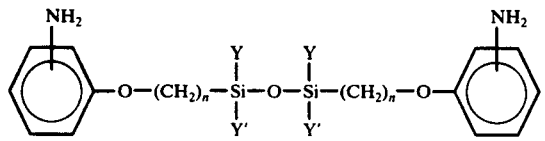

which is in the form of a liquid which is difficult to distill;

if X and Y are hydrolyzable substituents, the corresponding straight polymer is constituted by a chain of monomer units of formula

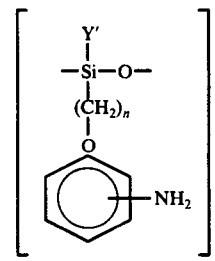

and is in the form of a non-distillable liquid or solid;

if X, Y and Y' are hydrolyzable substituents, the corresponding cross-linked polymer is formed of monomer units of formula

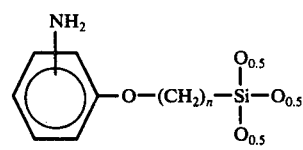

and is in the form of a non-distillable liquid or solid.

According to the invention, the process for the preparation of the aromatic amino silanes and their polymers consists in hydrogenating a silicon compound derived from nitrophenols in solution in a solvent, in the presence of a catalyst, at a temperature below 30° C.

The silicon compounds derived from nitrophenols are products of the general formula

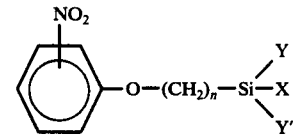

wherein $n$, X, Y and Y' have the same significance as above. Such compounds are described in French Patent Application No. 73.13881.

The process according to the invention leads generally to a mixture of aromatic amino silane and the corresponding polymer. It is however possible to orientate the reaction in one direction or the other; that is to say, that according to the product which it is desired to obtain, monomer or polymer, a more or less hydrolyzable compound is used. The less hydrolyzable compounds are those in which the silicon atom has 1, 2 or 3 alkoxy groups possessing a side chain, for example an ethyl group in the 2 position, which gives the compound great stability against hydrolysis. Thus, to obtain a large quantity of aromatic amino silane, it is advantageous to use a silicon compound derived from nitrophenols, the alkoxy group of which is constituted, for example, by a 2-ethyl-butoxy or 2-ethyl-hexoxy group.

The solvent utilized is preferably immiscible with water and dissolves the starting products and the products to be obtained. More particularly, aromatic solvents are used such as benzene, toluene, xylene. The quantity of solvent represents 1 to 2 times the quantity of silicon compound derived from nitrophenols.

The catalyst is a conventional catalyst for hydrogenation reactions, constituted by palladium or platinum fixed on a support, such as large-surface silica or charcoal, in an amount of 5% by weight. It is used in such quantity that the sum of support plus catalyst represents 3 to 10% weight of the silicon compound derived from nitrophenols.

The hydrogen is introduced continuously or in successive increments into the reaction medium at a pressure of the order of 2 to 5 bars. The introduction is continued until there is no more hydrogen absorption.

The reaction temperature below 30° C must be as low as possible to avoid hydrolysis when it is desired to obtain the aromatic amino silane; it is generally close to the ambient temperature. On the other hand, when it is desired to obtain a polymer, the temperature is preferably selected in the range close to 30° C.

When the reaction is terminated, the solvent is evaporated and the reaction products separated.

The invention also relates to the copolymers of aromatic amino silanes with conventional silanes in which the silicon atom has 1, 2 or 3 alkoxy groups having 1 or 2 carbon atoms, associated with methyl, ethyl or phenyl groups.

These copolymers are obtained either by hydrolysis of the two silanes, in accordance with any known process, or by addition of the conventional silane into the hydrogenation reaction medium.

These copolymers are a little less reactive than the polymers, which presents a certain advantage in certain applications.

All the aromatic amino silanes and the polymers and copolymers derived from the silanes having two or three hydrolyzable groups are utilizable especially for preparing grafted silicas and aluminas according to any known process. These grafted products are utilized in the fixing of various onzymes and catalysts.

The polymers and copolymers derived from the silanes having a hydrolyzable group are usable in the chemistry of dyestuffs and in the synthesis of polymers.

Examples of embodiments of the invention are given hereinafter by way of illustration and not limitation.

EXAMPLE 1

Into an autoclave there are introduced:

269 g of the compound

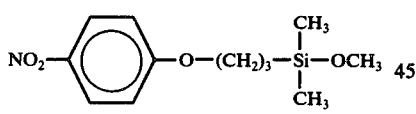

dissolved in 270 g of benzene, 13 g of palladium on charcoal (5% palladium).

Agitation is effected at ambient temperature and a rapidly absorbed hydrogen fraction is introduced under a pressure of 4 bars. Hydrogen is reintroduced until there is no further absorption.

The benzene is then expelled and one obtains 210 g of a non-distillable product of which the structure

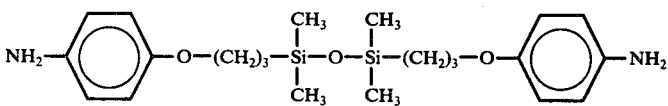

is confirmed by N.M.R. spectrography.

EXAMPLE 2

Example 1 is repeated but the starting compound is replaced by 285 g of the compound:

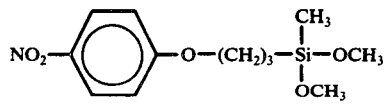

dissolved in 300 g of benzene.

After elimination of the benzene, the product is distilled and one obtains:

25 g of a liquid the boiling point of which is 142° C at 0.1 mm. Hg and the structure of which, confirmed by N.M.R. spectrography, is represented by the formula

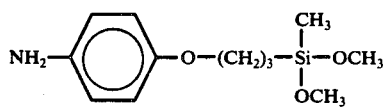

and 210 g of a non-distillable viscous liquid, the N.M.R. spectrography of which confirms that it is a polymer constituted by a chain of monomer units of formula

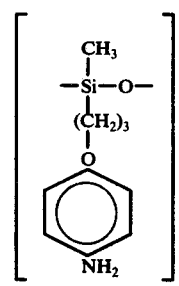

EXAMPLE 3

One operates as in Example 1, with 307 g of the compound

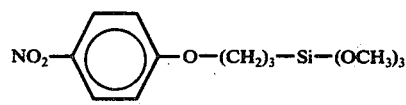

dissolved in 350 g of benzene.

One obtains 150 g of a liquid having the formula

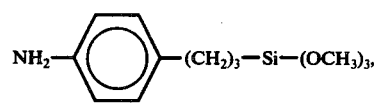

the boiling point of which is 187° C at 1 mm. Hg, and 130 g of a brown non-distillable viscous product having the formula

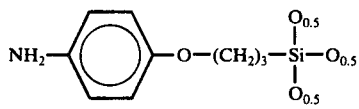

The linear product is utilized to graft silica.

A silica, surface area of 52 sq.m./g., pore volume 1 ml./g. and granulometry 100–200 μ, is dried for four hours at 150° C. 100 g. of the obtained dried silica are added to 200 ml. of a 5% solution of the linear compound in hexane. Heating is effected to boiling and maintained for four hours. The solid is decanted, washed with acetone and dried.

The grafted silica contains 2.35% of carbon, 0.25% of nitrogen and possesses an exchange capacity of 0.3 m.e.q./g.

EXAMPLE 4

One operates as in Example 1 with 307 g. of the compound

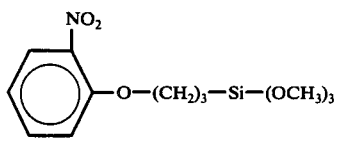

dissolved in 350 g. of toluene.

One obtains 145 g. of a liquid corresponding to the formula

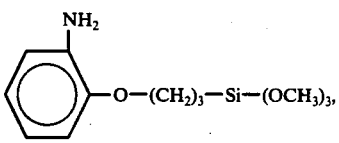

which boils at 140° C at 0.2 mm. Hg, and 140 g. of a non-distillable viscous product of formula

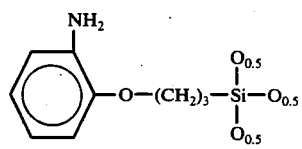

The distilled product is grafted as follows:

Into a balloon flask, there are introduced 345 ml. of a solution of sulphric acid of 120 g/l. Agitation is effected and a solution of sodium silicate of 220 g./l. of $SiO_2$ is added until a pH value of 3.5 is obtained, then 20 g. of distilled product are added, then again the sodium silicate solution is added up to pH 3.8.

A sol is obtained which is poured into a Keller balloon flask containing 10 l. of trichloroethylene and several drops of an alkyl sulphonate.

After 15 minutes of agitation, balls form on the walls of the balloon flask. Then one l. of ammoniated water at pH 9 are added. After several minutes, filtration is effected through a Buchner funnel, then drying is effected for three hours in an oven at 120° C.

Spherical balls of diameter below 250 microns are obtained.

The grafted silica contains 7.70% of carbon 0.95% of nitrogen.

EXAMPLE 5

Example 1 is repeated, with 340 g. of the compound

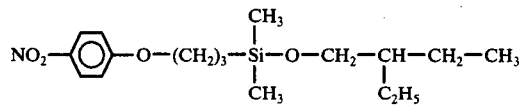

(Boiling point = 180° C at 0.5 mm. Hg) dissolved in 500 g. of benzene and 17 g. of the same catalyst. The hydrogen is introduced under a pressure of 5 bars.

By distillation, 240 g. of a liquid are obtained responding to the formula

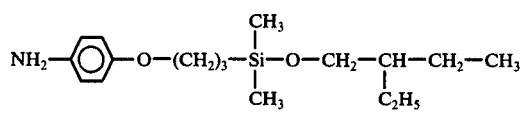

confirmed by N.M.R. and I.R. spectrography.

Its boiling point is 160° C at 0.5 mm. Hg.

After distillation, 40 g. remains of a non-distillable liquid the structure of which, determined by N.M.R. and I.R. spectrography, is identical with that of the product of Example 1.

By comparison with Example 1, one confirms that the presence of an ethyl-butoxy group in the place of the methoxy group has permitted orientating the reaction towards the monomer while avoiding hydrolysis.

I claim:

1. Polymers and copolymers formed of monomers at least one of which is an aromatic amino silane having the formula

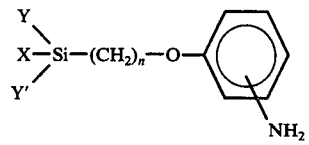

in which n is an integer with a value from 2 to 4, X represents a linear or branched alkoxy group having 1 to 8 carbon atoms, Y and Y', which may be identical or different from each other, represent a group selected from the group consisting of methyl, ethyl, phenyl, and a linear or branched alkoxy group having from 1 to 8 carbon atoms, other groups present in a copolymer being derived from monomers in the form of organo silanes having from 1 to 3 alkoxy groups attached to the silicon atom and associated with methyl, ethyl or phenyl groups on the silicon atom.

2. Polymers according to claim 1, represented by dimers of the formula

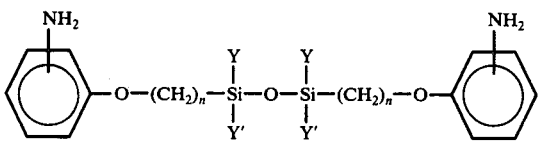

in which n is an integer with a value from 2 to 4, and y and y', which may be identical or different from each other, are selected from the group consisting of methyl, ethyl or phenyl.

3. Polymers according to claim 1, represented by linear polymers constituted from a chain of monomer groups of the formula

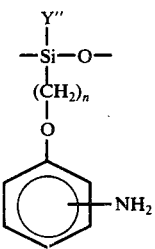

in which $n$ is an integer with a value from 2 to 4, $y''$ represents a group selected from the group consisting of methyl, ethyl or phenyl.

4. Polymers according to claim 1, represented by cross-linked polymers formed from monomer groups of the formula

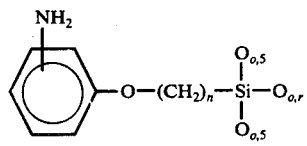

in which $n$ is an integer with a value from 2 to 4.

5. Polymers according to claim 1, represented by copolymers having at least one monomer group like that of claim 9 and at least one monomer in the form of an organo silane having from 1 to 3 alkoxy groups associated with methyl, ethyl or phenyl groups on the silicon atom.

6. The method for the preparation of polymers according to claim 1, in which an aromatic nitrated silane of the formula

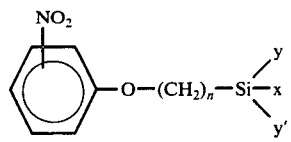

in which: $n$ is an integer with a value from 2 to 4, $x$ represents an alkoxy group having from 1 to 8 carbon atoms, $y$ and $y'$, which may be identical or different from each other, are selected from the group consisting of methyl, ethyl, phenyl, and a linear or branched alkoxy group having from 1 to 8 carbon atoms is placed in solution in a solvent, hydrogenated in the presence of a catalyst, at a temperature below 30° C alone or in the presence of another organo silane monomer having from 1 to 3 alkoxy groups associated with methyl, ethyl or phenyl groups on the silicon atom.

7. Polymers according to claim 1 represented by copolymers having at least one monomer group like that of claim 10 and at least one monomer in the form of an organo silane having from 1 to 3 alkoxy groups associated with methyl, ethyl or phenyl groups on the silicon atom.

8. Polymers according to claim 1 represented by copolymers having at least one monomer group like that of claim 11 and at least one monomer in the form of an organo silane having from 1 to 3 alkoxy groups associated with methyl, ethyl or phenyl groups on the silicon atom.

9. The method as claimed in claim 6 which includes the step of polymerizing the resulting amino silane through hydrolysis of alkoxy groups to form homopolymers or copolmers with another organo silane monomer having from 1 to 3 alkoxy groups associated with methyl, ethyl or phenyl groups on the silicon atom.

* * * * *